(12) United States Patent
Hadfield

(10) Patent No.: US 11,944,667 B2
(45) Date of Patent: Apr. 2, 2024

(54) METHODS OF MAKING A WOUND TREATMENT COMPOSITION

(71) Applicant: Biotherapy Services Limited, Windsor (GB)

(72) Inventor: Janet Hadfield, Windsor (GB)

(73) Assignee: Biotherapy Services Limited, Windsor (GB)

(*) Notice: Subject to any disclaimer, the term of this patent is extended or adjusted under 35 U.S.C. 154(b) by 0 days.

(21) Appl. No.: 16/818,839

(22) Filed: Mar. 13, 2020

(65) Prior Publication Data
US 2020/0215164 A1 Jul. 9, 2020

Related U.S. Application Data

(63) Continuation of application No. PCT/GB2019/053460, filed on Dec. 6, 2019.

(30) Foreign Application Priority Data

Dec. 7, 2018 (GB) ..................................... 1819987

(51) Int. Cl.
| | |
|---|---|
| A61K 38/36 | (2006.01) |
| A61K 31/341 | (2006.01) |
| A61K 35/16 | (2015.01) |
| A61K 35/20 | (2006.01) |
| A61P 17/02 | (2006.01) |

(52) U.S. Cl.
CPC ............ *A61K 38/36* (2013.01); *A61K 31/341* (2013.01); *A61K 35/16* (2013.01); *A61K 35/20* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 5,811,279 A | 9/1998 | Kaetzsu et al. | |
| 5,945,103 A | 8/1999 | Hanada et al. | |
| 2001/0055621 A1* | 12/2001 | Baugh | A61M 1/3616 424/530 |
| 2005/0265989 A1* | 12/2005 | Manseth | A61K 35/60 424/94.65 |
| 2008/0280343 A1* | 11/2008 | Pawlak | A61P 7/04 435/214 |
| 2010/0226902 A1* | 9/2010 | Fylling | A61L 24/0005 424/93.72 |
| 2015/0030578 A1 | 1/2015 | Releford, Jr. et al. | |
| 2015/0079067 A1 | 3/2015 | Tsai | |

FOREIGN PATENT DOCUMENTS

| | | | | |
|---|---|---|---|---|
| CA | 2529905 A1 | | 6/2007 | |
| CN | 107198893 | * | 9/2017 | ........... B01D 17/038 |
| EP | 2898909 A1 | | 7/2015 | |
| JP | 11-228443 A | | 8/1999 | |
| KR | 10-2001-0071577 A | | 7/2001 | |
| KR | 10-1313755 A | | 10/2013 | |
| WO | 2004084825 A2 | | 10/2004 | |
| WO | 2007/005820 A1 | | 1/2007 | |
| WO | 2007127834 A2 | | 11/2007 | |
| WO | 2010005557 A2 | | 1/2010 | |
| WO | 2010122548 A2 | | 10/2010 | |
| WO | 2017000826 A1 | | 1/2017 | |

OTHER PUBLICATIONS

Arthrex Angel System, Angel Concentrated Platelet Rich Plasma (cPRP) System, Operator's Manual, May 2020, 116 pages, retrieved from the internet: https://www.arthrex.com/resources/manuals-troubleshooting/84RzEyTYDUK2QgFy7QBoTg/angel-concentrated-platelet-rich-plasma-cprp-system-operators-manual (Year: 2020).*
Arthrex, The Angel® cPRP System, Customized Cellular Concentrations of Platelet-Rich Plasma, 2019, 12 pages, retrieved from the internet: https://www.arthrex.com/resources/brochures/CfVFVseLk02xlwFEK9V6Pg/the-angel-cprp-system-for-customized-cellular-concentrations-of-platelet-rich-plasma (Year: 2019).*
UCSF Health, Platelet Count, 3 pages, retrieved from the internet Oct. 21, 2020:https://www.ucsfhealth.org/medical-tests/003647#:~:text=The%20normal%20number%20of%20platelets,400%20%C3%97%20109%2FL. (Year: 2020).*
Etulain et al, Scientific Reports (2018) 8:1513, pp. 1-15 (Year: 2018).*
Nair et al., British Journal of Haematology, Jul. 2017; 178(1): 119-129, published online Jun. 4, 2017 (Year: 2017).*
Reddoch et al., Shock, vol. 41, Supplement 1, pp. 54-61, 2014 (Year: 2014).*
Sternberger et al. J. clin. Path. (1948), 1, 229, pp. 229-231 (Year: 1948).*

(Continued)

*Primary Examiner* — Evelyn Y Pyla
(74) *Attorney, Agent, or Firm* — Gavrilovich, Dodd & Lindsey LLP

(57) ABSTRACT

The present invention provides a method of making a wound treatment composition, wherein the method comprises; i) fractionating a whole blood sample into multiple samples including a platelet rich plasma (PRP) sample, a platelet poor plasma (PPP) sample and a erythrocyte sample, wherein the PRP sample has a haematocrit level of 1-10%, ii) processing a portion of the PPP and/or PRP sample to facilitate cleavage of autologous pro-thrombin present in the PPP and/or PRP to produce autologous thrombin, and iii) combining the PRP sample with a portion of the PPP sample and a portion of the thrombin produced in step (ii) to produce the wound treatment composition; wherein step ii) is performed at less than 15° C. In preferred embodiments the PRP has a haematocrit level of 2 or 8%. Wound treatment compositions produced by the methods are also provided as are compositions for use in treating chronic and acute wounds.

9 Claims, 9 Drawing Sheets

(56) References Cited

OTHER PUBLICATIONS

1. Kumar et al., Whole Blood Thrombin: Development of a Process for Intra-Operative Production of Human Thrombin (JECT. 2007; 39:18-23 (Year: 2007).*
2. Kumar et al., Autologous Thrombin: Intraoperative Production From Whole Blood (JECT. 2008; 40:94-98 (Year: 2008).*
Biotherapy Services: "Rapid Biodynamic PRP Haematogel Chronic Wound Care Treatment", Aug. 22, 2016, retrieved from the Internet: URL:https://www.biotherapyservices.com/wp-content/uploads/2017/11/prp-wound-therapies-rapid-biodynamic-haematogel-ifu.pdf [retrieved Sep. 17, 2018].
Feeney, Graham, Office Action, Application No. GB1819987.7, United Kingdom Patent Office, dated May 20, 2019.
Hubbard, Ryan et al., "Arthrex Angel System Parameters for High Platelet, Low Erythrocyte, Low Neutrophil Platelet-Rich Plasma: A Quality Control Study", PM&R, vol. 7, No. 9, 2015.
Schnack, Anne, Search Report, U.S. Appl. No. 18/165,972, European Patent Office, dated Sep. 24, 2018.
Tambella et al., "Platelet-rich plasma to treat experimentally-induced skin wounds in animals: A systematic review and meta-analysis", PLoS One, vol. 13, No. 1, Jan. 11, 2018, pp. 1-26.
Ruiz Fernandez, Jose, International Preliminary Report on Patentability and Written Opinion, European Patent Office, PCT/GB2019/053460, dated Aug. 31, 2020.
"Arthrex Angel Systems: Indication-specific PRP and PRF gel preparations," URL:http://www.mrmedikal.com/content/ArthrexAgnelSystem.pdf, Jan. 1, 2014.
"Arthrex Angel System (TM) Indication-Specific PRP Preparations," URL:https://www.bonameda.com/sites/sophimeda/fiiles/news/angel_system.pdf, Feb. 4, 2020.
Cravens et al., "Comparison or mechanical compressive properties of commercial and autologous fibrin glues for tissue engineering applications," Clinical Biomechanics, vol. 49, pp. 34-39, Aug. 2017.
Degen et al., "Commercial Separation Systems Designed for Preparation of Platelet-Rich Plasma Yield Differences in Cellular Composition," HSS Journal, vol. 13, No. 1, pp. 75-80, Aug. 19, 2016.
Everts et al., "Platelet-rich plasma and platelet gel: a review," J. of Amer. Soc. of Extra-Corporeal Technol., vol. 38, No. 2, pp. 174-187, 2006.
Christensen, Jette, International Search Report, PCT/GB2019/053460, European Patent Office, dated Feb. 19, 2020.
Velier et al., "Production of platelet-rich plasma gel from elderly patients under antithrombotic drugs: Perspectives in chronic wounds care," Platelets, vol. 29, No. 5, pp. 496-503, Aug. 14, 2017.
Arthrex Angel System, Angel(R) Concetrated Platelet Rich Plasma (cPRP) System—Operator's Manual, Jun. 2020.
Arthrex Angel System, www.arthrex.com Arthrex GmbH, 2017 (https://www.bonameda.com/sites/sophimeda/files/news/angel_system.pdf, Jan. 1, 2017, Search date: Aug. 2, 2021.
Korean Patent Office, Office Action, Application No. 9-5-2021-062887156, dated Sep. 8, 2021.
Saudi Arabia Patent Office, Office Action, Application No. 119400779, dated Mar. 3, 2021.
Japanese Patent Office, Office Action, Application No. 2021-532910 dated Dec. 6, 2021.
Saudi Arabia Patent Office, Office Action, Application No. 119400779, dated Sep. 5, 2021.
"Arthrex Angel Systems: Indication-specific PRP and PRF gel preparations," 2015.

* cited by examiner

METHODS OF MAKING A WOUND TREATMENT COMPOSITION

CROSS REFERENCE TO RELATED APPLICATIONS

The application is a continuation of International Application Serial Number PCT/GB2019/053460, filed Dec. 6, 2019, which claims priority to Great Britain Application Number 1819987.7, filed Dec. 7, 2018, the disclosure of which are incorporated herein by reference in their entirety.

FIELD OF THE INVENTION

The present invention relates to a method of producing a wound treatment composition wherein the treatment comprises platelet rich plasma.

BACKGROUND OF THE INVENTION

Wounds are commonly caused by physical injury to the body and can also be caused by infectious diseases or underlying conditions. Wounds are generally classified as either chronic or acute. Chronic wounds do not proceed through the normal phases of wound healing and are commonly associated with conditions such as diabetes mellitus. Acute wounds are generally inflicted suddenly and heal at a predictable and expected rate via the normal phases of wound healing.

The need to treat wounds quickly and efficiently is of great importance within the medical practice. For example, non-healing chronic wounds are a significant source of mortality and morbidity in diabetic patients, and often if a wound cannot be treated then the limb will have to be amputated. As the incidence of diabetes is increasing there is an increasing need to develop effective treatment for chronic wounds. Currently in the UK 2.2 million chronic wounds are treated annually at a cost of £5.1-5.3 bn per annum.

The present invention relates to a method of producing a platelet rich plasma (PRP) containing wound treatment composition. This composition is especially suited to topical application to chronic or acute wounds.

The wound treatment composition is produced from a whole blood sample and utilises and enhances the wound healing properties of various components of the blood. Whole blood comprises three main types of cell—erythrocytes, leukocytes and thrombocytes (platelets), suspended in plasma. Erythrocytes are the red blood cells, which contain haemoglobin and transport oxygen around the body. Leukocytes are the white blood cells which are involved in combating infection through innate and adaptive immune responses and thrombocytes commonly known as platelets contribute to haemostasis/clotting which stops bleeding at a site of damage.

Platelets aid in the wound healing process by helping to stop bleeding by forming a platelet plug. When a site of damage is detected the platelets begin to adhere to the site and are activated to release granular material by an agonist such as thrombin. Once granular activation occurs this stimulates the release of growth factors which stimulates the formation of new tissue and initiates the inflammatory stage of wound healing.

PRP based wound treatments are currently known within the art. However, the present inventors have surprisingly found that PRP can be produced with various haematocrit levels which are particularly suitable for the treatment of chronic or acute wounds. More specifically PRP with a haematocrit level of approximately 8% retains substantially all of the leukocytes from the whole blood sample and has been shown to be particularly effective in treating acute wounds. PRP produced with a haematocrit level of approximately 2% is substantially free of leukocytes and has been shown to be particularly effective at treating chronic wounds. Further the present method also allows the PRP to be produced with a high concentration of platelets and it has been found that a platelet level of 4-6 times the baseline (i.e. the concentration of platelets found in a patient's blood) is most suitable for use in treating wounds. Commercial separation systems designed for preparation of PRP fractions from whole blood were compared by Degen et al (2016) The musculoskeletal Journal of Hospital for Special Surgery (HSSJ) vol 13: 75-80, herein incorporated by reference.

The invention described herein provides a method to produce a wound treatment gel by combining the PRP with autologously-derived thrombin. In this method both the PRP and the thrombin are derived from the same whole blood sample and as such the gel is a fully autologous wound care composition. Other similar wound care gels have been produced; however these use bovine thrombin which could result in complications such as an immunological response and transmission of infections such as bovine spongiform encephalopathy. Further, bovine thrombin is not approved for use in countries such as the UK. By combining the PRP with autologous thrombin the platelets become activated consequently releasing growth factors, cytokines, and chemokines as well as activating fibrinogen in the plasma causing the formation of the fibrin matrix scaffold. The growth factors help to stimulate the wound healing process and the production of the fibrin extracellular matrix results in the gel consistency.

The present inventors have surprisingly found that production of the autologous thrombin at low temperature significantly improves the consistency of the wound treatment gel that is produced. The gel produced has an almost solid consistency which allows it to hold shape for at least 10 minutes and within the wound application, will stay intact and insite for greater than 48 hours. This effectively provides a matrix for the integration of tissue into this autologous scaffold.

To help further stabilise the gel consistency ascorbic acid (Vitamin C) can be incorporated in the composition. The ascorbic acid also provides further benefits such as scavenging free radicals, protecting the tissue, enabling collagen synthesis and is anti-inflammatory.

The present method provides an autologous wound treatment composition wherein the composition can either comprise a high proportion of leukocytes or can be substantially free of leukocytes depending on the type of wound to be treated. As such using this method allows the leukocyte level to be tailored to the type of wound to be treated and results in a quicker and more effective wound treatment composition. The composition has been used in the treatment of chronic wounds in diabetic patients, and in the pilot cohort of n15 patients over the course of the treatment the average reduction in wound volume was >75%. The average time taken for wound closure to be achieved was 17.9 days with approximately 5 treatments of the wound treatment composition. This treatment clearly provides a surprisingly improved treatment for wounds.

The listing or discussion of an apparently prior-published document in this specification should not necessarily be taken as an acknowledgement that the document is part of the state of the art or is common general knowledge.

SUMMARY OF THE INVENTION

It has been surprisingly found that by producing a PRP sample with haematocrit levels between 1-10%, wound treatment compositions can be produced which are particularly effective in either acute or chronic wounds depending on the haematocrit levels used. In particular a PRP sample with a haematocrit level of approximately 8%, wherein the PRP comprises a high proportion of leukocytes, has been found to be effective in treating acute wounds. Whereas a PRP sample with a haematocrit level of approximately 2%, wherein the PRP is substantially free of leukocytes, has been found to be effective in treating chronic wounds. Further the present inventors have found that the wound treatment compositions with different haematocrit levels can be used sequentially during the treatment of a wound. For example when treating a chronic wound the wound can be debrided to induce an acute phase this wound is first treated with a composition with an 8% haematocrit level. Upon subsequent treatments of the wound a composition with a 2% haematocrit level is used. The combination of these treatments has been shown to be particularly effective in achieving wound closure and rapid wound healing. In trials a reduction of wound volume of 75% was achieved over an average of 5 treatments and 17.9 days. It is to be understood that references herein to wound treatment compositions with a certain percentage haematocrit are references to compositions produced from PRP preparations produced to the appropriate haematocrit percentage, prior to the introduction of excipients such as the autologous thrombin and ascorbic acid and may not necessarily indicate the final haematocrit percentage in the wound treatment composition prepared using the methods described herein.

To form the wound treatment composition of the invention the PRP samples are combined with autologous thrombin (thus the thrombin has been derived from the same source as the PRP). This produces a composition with a gel consistency which is particularly suitable for topical application to wounds. The present inventors have surprisingly found that the temperature at which the autologous thrombin is produced can affect the consistency of the final wound composition. Autologous thrombin is produced by cleaving prothrombin into thrombin. When this process is carried out at a temperature of less than 15° C. the resultant gel that is obtained from the combination of the thrombin and the PRP has beneficial qualities. For example, the gel has an almost solid consistency which allows it to maintain its shape for approximately ten minutes when removed from a mould and has been shown to remain intact, in situ for greater than 48 hours, effectively filling cavernous catastrophic wounds, and providing an effective matrix for the long acting release of growth factors and cellular proteins. In comparison, previous wound care gels only maintain their shape for up to approximately 60 seconds. Without wishing to be bound by theory, it is hypothesised that the more solid consistency allows the gel to be retained within the wound for a longer time before dissolving and as such it can release growth factors over a prolonged period. These properties lead to improved wound healing, as can be seen from the examples provided herein.

Further, the more solid consistency of the gel has been found to be particularly beneficial in treating wounds where significant tissue volume has been lost. In these instances, since the gel can retain its shape, it provides a scaffold within the wound around which tissue regeneration can occur.

Therefore one aspect of the present invention relates to a method of making a wound treatment composition, wherein the method comprises; i) fractionating a whole blood sample into multiple samples including a platelet rich plasma (PRP) sample, a platelet poor plasma (PPP) sample and a erythrocyte sample, wherein the PRP sample has a haematocrit level of 1-10%, ii) processing a portion of the PPP and/or PRP sample to facilitate cleavage of autologous pro-thrombin present in the PPP and/or PRP to produce autologous thrombin, and iii) combining the PRP sample with a portion of the PPP sample and a portion of the thrombin produced in step (ii) to produce the wound treatment composition; and wherein step ii) is carried out at a temperature of less than 15° C.

In an embodiment, it is envisaged that step iii) of the first aspect may also be carried out at a temperature of less than 15° C.

A second aspect of the invention comprises a wound treatment composition obtainable by the method of the first aspect.

A further aspect of the invention provides a method of treating wounds in a subject by administering a wound treatment composition obtainable by the method according to the first aspect of the invention.

The invention further provides a wound treatment composition according to the second aspect for use in medicine, more particularly for use in treating a wound.

In order that the invention may be more clearly understood embodiments thereof will now be described by way of example with reference to the accompanying figures.

DETAILED DESCRIPTION OF THE INVENTION

In a first aspect of the present invention there is provided a method of making a wound treatment composition, wherein the method comprises;
i) fractionating a whole blood sample into multiple samples including a platelet rich plasma (PRP) sample, a platelet poor plasma (PPP) sample and a erythrocyte sample, wherein the PRP sample has a haematocrit level of 1-10%,
ii) processing a portion of the PPP and/or PRP sample to facilitate cleavage of autologous pro-thrombin present in the PPP and/or PRP to produce autologous thrombin, and
iii) combining the PRP sample with a portion of the PPP sample and a portion of the thrombin produced in step (ii) to produce the wound treatment composition; and
wherein step ii) is carried out at a temperature of less than 15° C.

As used herein, the term "whole blood" is one of the art and refers to a composition which comprises plasma, erythrocytes, leukocytes and platelets. Thus, whole blood may be a fresh blood sample drawn from an individual containing all the natural components. The whole blood sample may also comprise a citrate or other suitable buffer to help prevent coagulation of the sample. It is envisaged that the buffer will be pharmacologically acceptable.

The term "platelet rich plasma (PRP)" refers to plasma which contains a high proportion or concentration of platelets (i.e. higher than whole blood); it is also substantially free of erythrocytes. The PRP is prepared by fractionating a whole blood sample (for example by centrifugation) and contains platelets at a concentration that is higher than that found in the whole blood sample. According to the first aspect of the present invention the PRP may contain more than $600 \times 10^9$ platelets per litre, or more than $800 \times 10^9$ platelets per litre, or more than $1000 \times 10^9$ platelets per litre, or more than $1200 \times 10^9$ platelets per litre, or more than $1400 \times 10^9$ platelets per litre, or more than $1600 \times 10^9$ platelets per litre, or more than $1800 \times 10^9$ platelets per litre, or more than $2000 \times 10^9$ platelets per litre, or more than $2200 \times 10^9$ platelets per litre, or more than or more than $2400 \times 10^9$ platelets per litre. Further, according to the first aspect of the present invention the PRP may contain 600 to $2400 \times 10^9$ platelets per litre, or 800 to $2200 \times 10^9$ platelets per litre, or 1000 to $2000 \times 10^9$ platelets per litre, or 1200 to $1800 \times 10^9$ platelets per litre, or 1400 to $1600 \times 10^9$ platelets per litre, or any combination thereof. The "platelet poor plasma (PPP)" is produced by fractionating a whole blood sample and refers to the plasma which contains a low proportion of platelets, for example less than $1 \times 10^9$ platelets per litre, or less than $1 \times 10^8$ platelets per litre, or less than $1 \times 10^7$ platelets per litre.

Figure 7:
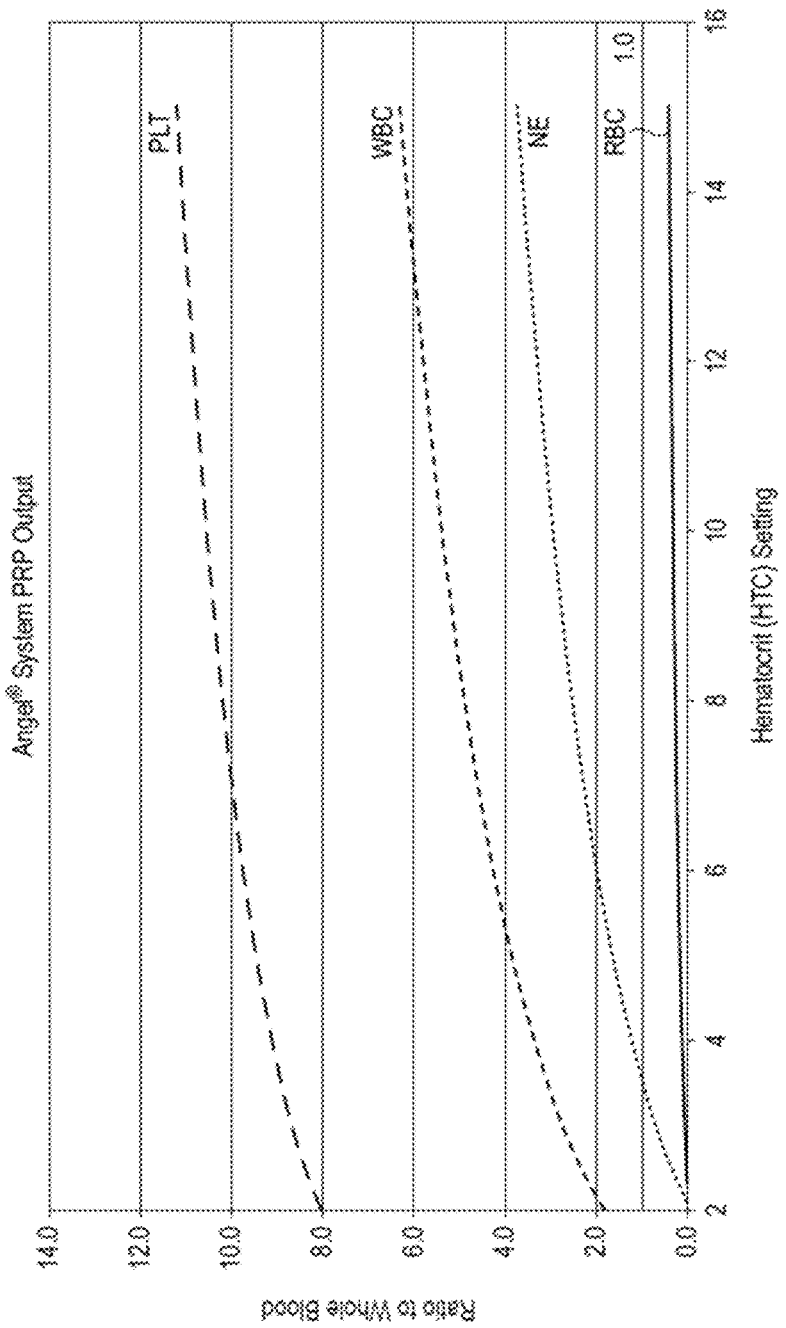
FIG. 7 provides an illustration of the PRP output of the Arthrex® Angel® System used in the examples. In order to evaluate the difference between the Arthrex® Angel® System PRP output and whole blood, the Arthrex® Angel® System PRP was prepared from the venous blood of 6 healthy donors at hematocrit settings of 2%, 5%, 7%, 10% and 15%. The concentration of platelets, white blood cells (WBC) and neutrophils (NE) were measured with a standard complete blood count (CBC).

As is explained in more detail below, it is envisaged that the optimal platelet level in the PRP will be obtained either directly from fractionation of the whole blood to produce the PRP in step i) or following dilution of the PRP with PPP following step i). The optimal platelet concentration in the PRP is thus obtained prior to addition of the autologous thrombin (with optional ascorbic acid). An illustration of the output from the Arthrex® Angel® system is provided in FIG. 7.

The term "autologous thrombin" as used herein refers to thrombin which has been derived from the same whole blood sample as the PRP has been derived.

The wound treatment composition produced according to the first aspect of the invention may comprise from 200 to $2400 \times 10^9$ platelets per litre, or from 400 to $2400 \times 10^9$ platelets per litre, 600 to $2400 \times 10^9$ platelets per litre, or 800 to $2200 \times 10^9$ platelets per litre, or 1000 to $2000 \times 10^9$ platelets per litre, or 1200 to $1800 \times 10^9$ platelets per litre, or 1400 to $1600 \times 10^9$ platelets per litre.

In a particular embodiment of the first aspect of the invention the method further comprises the step of adding ascorbic acid (Vitamin C) to the wound treatment composition contemporaneously with, prior to, or after addition of the thrombin. The ascorbic acid is added at a concentration of between 0.5 mM and 5 mM, preferably between 2 mM and 4 mM, most preferably between 2.5 mM and 3 mM. In a preferred embodiment of the first aspect of the invention the ascorbic acid (Vitamin C) is added to the PRP sample.

There are a number of methods known in the art which are suitable for facilitating cleavage of prothrombin into thrombin and which are appropriate for use in the present invention. In a particular embodiment of the first aspect of the invention, stage ii) of the method comprises contacting the portion of the PPP sample and/or the PRP sample with a composition comprising calcium chloride and/or ethanol. A solution comprising calcium chloride in ethanol is particularly suitable for facilitating cleavage of prothrombin into thrombin. The solution may contain between approximately 5 to 20% w/v calcium chloride, or between approximately 8 to 15% w/v calcium chloride, preferably the solution contains 10% w/v calcium chloride. The calcium chloride may be present in a solution comprising ethanol, wherein the solution may contain between approximately 10 to 30% v/v ethanol, or between approximately 10 to 20% v/v ethanol, preferably the solution contains approximately 17% v/v ethanol. There are commercially available kits which are suitable for processing a portion of the PPP and/or PRP sample to facilitate cleavage of autologous pro-thrombin present in the PPP and/or PRP to produce autologous thrombin; non-limiting examples of such kits include the Biotherapy Services ActivAT kit and Arthrex Thrombinator.

In the first aspect of the invention step ii) is performed at a temperature of less than 15° C. In particular, step ii) may be performed at a temperature from 2° C. to 15° C., 4° C. to 15° C., 6° C. to 15° C., 8° C. to 15° C., 10° C. to 15° C. or 12° C. to 15° C. In this embodiment the portion of the PPP and/or the PRP sample and the solutions required for the prothrombin cleavage reaction are cooled to less than 15° C. Typically, this may be achieved by storing the solutions prior to and during the reaction on ice. This results in the cleavage reaction occurring at a lower temperature. When the thrombin is combined with the PRP, the platelets become activated and results in the formation of the gel. Since higher temperature are known to increase reaction kinetics, it is highly surprising that performing the cleavage reaction at a lower temperature produces a thrombin sample which results in a more solid and effective gel. For the avoidance of doubt, it is envisaged that step i) of the first aspect would typically be performed at room temperature. Suitable methods to fractionate a whole blood sample are known within the art. A particular feature of the invention is that centrifugation is used to fractionate the whole blood sample. During the fractionation stage the centrifugation may be performed in two stages. An initial centrifugation stage may be used to separate the erythrocytes from the other components followed by a second centrifugation stage which helps to fractionate the platelets and form the PRP. The initial centrifugation stage may be performed at between 3,000 and 4,500 rpm, preferably between 3,200 and 4,000 rpm, more preferably at 3,700 rpm. The second centrifugation stage may be performed at between 2,000 and 3,500 rpm, preferably between 2,500 and 3,000 rpm, more preferably at 2,700 rpm. Such centrifugation steps may preferably be carried out using the Arthrex® Angel® system.

During the fractionation process the PRP sample will sub-fractionate producing PRP which contains a high concentration of leukocytes and PRP which contains a low concentration of leukocytes. Therefore, PRP can be produced comprising different levels of leukocytes. As used herein the term "haematocrit level" refers to the approximate amount of leukocytes which are present in the PRP fractionated from the whole blood sample.

To produce PRP samples having different haematocrit levels a sensor may be used which can differentiate between the PPP sample, PRP sample and the erythrocyte sample. The sensor can also differentiate between PRP samples which are high in leukocytes and samples low in leukocytes. Suitable sensors include LED sensors. Further, there are a number of commercially available systems which are suitable for producing PRP with a specified haematocrit level including the Magellan® Autologous Platelet Separator, Biomet GPS® Platelet concentration System and Arthrex® Angel® system.

By producing a PRP sample with different haematocrit levels it is possible to alter the amount of leukocytes present in the PRP. To form PRP comprising a high proportion of leukocytes, wherein more than 80% of the total leukocytes from the whole blood sample will be present in the PRP, the PRP should be produced with a higher haematocrit level, for example between a 5 to 10% haematocrit level, preferably between a 7 to 9% haematocrit level. To form PRP which is substantially free from leukocytes, wherein less than 10% of the total leukocytes of the whole blood sample will be present in the PRP, the PRP should be produced with a lower haematocrit level, for example between a 1 to 5% haematocrit level, preferably between a 1 to 3% haematocrit level.

A PRP sample produced with a haematocrit level of 2% will be substantially free from leukocytes, more specifically less than 10% of the total leukocytes of the whole blood sample will be present in the PRP sample, preferably less than 5%, more preferably less than 2%, most preferably less than 1%. A PRP produced with a haematocrit level of 2% will be substantially free from leukocytes, for example the PRP may contain less than $12 \times 10^8$ leukocytes per litre, or less than $6 \times 10^8$ leukocytes per litre, or less than $3 \times 10^8$ leukocytes per litre, or less than $12 \times 10^7$ leukocytes per litre, or less than $6 \times 10^7$ leukocytes per litre, or less than $3 \times 10^7$ leukocytes per litre. In a particular embodiment of the present invention the PRP sample has a haematocrit level of approximately 2%. In other embodiments of the present invention the PRP sample may have a haematocrit level of approximately 1, 1.5, 2.5, 3, 3.5, 4 or 4.5%.

In contrast a PRP produced with a haematocrit level of approximately 8% will comprise the majority of the leukocytes present from the whole blood sample; more specifically more than 80% of the total leukocytes from the whole blood sample will be present in the PRP, preferably more than 90%, more preferably more than 95%. A PRP produced with a haematocrit level of 8% will comprise the majority of the leukocytes present from the whole blood sample, for example it may comprise more than $1 \times 10^9$ leukocytes per litre, or more than $3 \times 10^9$ leukocytes per litre, or more than $5 \times 10^9$ leukocytes per litre, or more than $10 \times 10^9$ leukocytes per litre. Preferably a PRP produced with a haematocrit level of 8% may comprise between approximately $1 \times 10^9$ to $15 \times 10^9$ leukocytes per litre, more preferably it may comprise between approximately $3 \times 10^9$ to $12 \times 10^9$. As such in a particular embodiment of the present invention the PRP sample has a haematocrit level of 8%. In other embodiments of the present invention the PRP sample may have a haematocrit level of approximately 5.5, 6, 6.5, 7, 7.5, 8.5, 9 or 9.5%.

Figure 6:
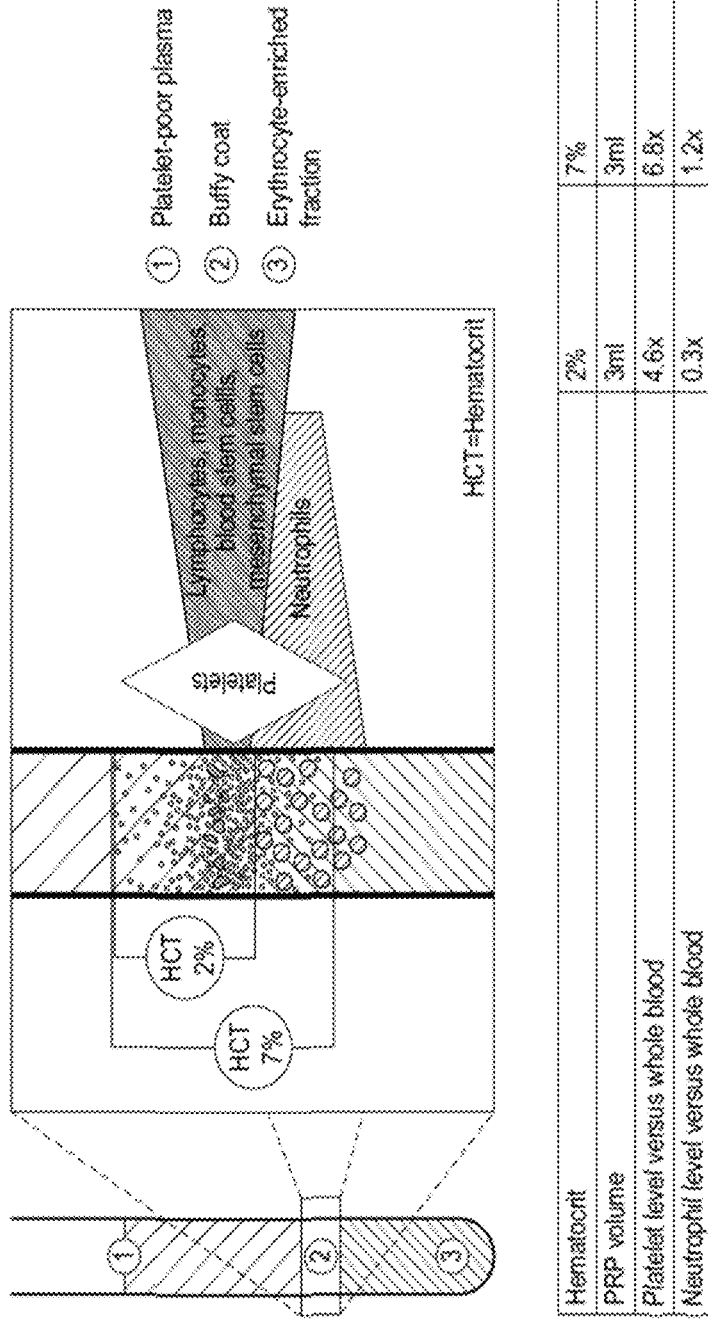
FIG. 6 provides an illustration of the result of fractionating whole blood according to the methods of the invention using the Arthrex® Angel® system. This illustrates the cell types generally found in each fraction and the changing haematocrit level from the PPP, through the PRP to the erythrocyte portion. Approximate platelet levels are provided for haematocrit levels of 2% and 7%.

As will be appreciated by a person of skill in the art, the "haematocrit" level is a direct visual measurement of the concentration of red blood cells in the sample. While this is not a direct measurement of the level of leukocycles or platelets in the blood sample, in the context of human blood fractionation it directly correlates with the level of leukocycles and/or platelets in the sample. This is illustrated in FIG. 6, which shows the gradient of haematocrit in whole blood fractionated using the Arthrex Angel System as described herein. In the art, the haematocrit level is commonly used as a convenient measurement that enables repeatable measurement of constituents of blood following fractionation. This is the means by which collection of blood fractions of desired composition may be automated. Thus, in the art, the haematocrit measurement allows automated collection of concentrated platelet samples with desired levels of platelets. The haematocrit level enables collection of PRP fractions both manually and by computer as the level of haemoatcrit is clearly distinguishable and is repeatable and predictable. More invasive means of directly measuring platelet level would not be appropriate in the context of the invention, which is a method intended to quickly produce a wound treatment composition that can be rapidly applied to the patient's wound. Measuring haematocrit does not require any direct contact with the blood sample or the addition of any factors as it can be simply performed with an optical measurement (detecting differences in light absorption), as is performed by the devices used in the examples. Thus, haematocrit is a surrogate marker of platelet level and its meaning and purpose would be readily appreciated by a person of skill in the art.

The present inventors have further found that there is an optimum level of platelets to be present in the PRP sample. The most effective PRP platelet concentration was found to be between 4 and 6 times the baseline platelet level, wherein the baseline platelet level is that found in the whole blood sample. Therefore, if the PRP sample contains more than between 4 and 6 times the baseline platelet level then the PRP sample can be diluted using the PPP sample. This will ensure that the PRP sample contains 4 and 6 times the baseline platelet level, prior to the inclusion of the autologous thrombin and excipients such as asorbic acid.

Thus, as will be appreciated in view of the above, the principle purpose of combining a portion of the PPP sample with the PRP sample at step iii) of the method of the invention, prior to combining with activated thrombin, is to achieve a PRP sample with an optimal platelet level. Thus the PPP may be used to dilute the PRP (the concentrated PRP) before further processing. The optimum platelet level in the PRP prior to combining with the thrombin will depend on the patient and on the wound to be treated. As will be understood by a person of skill in the art, some individuals exhibit higher levels of platelets for example due to natural disposition or disease. Conversely, some individuals will exhibit lower levels of platelets for example due to natural disposition or disease. The methods of the invention and the wound treatment composition manufactured by the methods may thus be tailored to the patient according to the natural levels of platelets in the patient's blood, which effects the volume of concentrated PRP generated in the first step of the method of the invention. As is explained above, it is preferred that the level of platelets in the PRP prior to addition of thrombin (and optionally ascorbic acid) will be approximately between 4 and 6 times the baseline platelet level in that individual patient. In some instances, the PRP produced in step i) of the method of the invention will have a platelet level that is acceptable for continued processing (for example if the patent has low platelet levels) but in most instances the PRP produced in step i) will have a higher than desired platelet level. In this instance the PPP may be used to dilute the PRP to the desired platelet level.

As would be understood by a person skilled in the art, the concentration of platelets in the PRP produced by the method is independent of the volume of concentrated PRP that is produced in the method, for example by using the Arthrex® Angel® system. Rather, the volume is indicative of the amount of platelets in the whole blood sample prior to processing. Thus, the PRP is produced at a nearly fixed concentration of platelets but the volume of PRP varies. The concentration of platelets in the PRP produced by the Arthrex® Angel® system is in the region of $3600 \times 10^9$ platelets per litre. For example, a patient having $100 \times 10^9$ platelets per litre in their blood will generate approximately 1 ml concentrated PRP, this is then diluted back to 6 ml by the addition of PPP and will produce a diluted PRP solution with approximately $600 \times 10^9$ platelets per litre (6× baseline). A patient having approximately $400 \times 10^9$ platelets per litre in their blood will generate approximately 4 ml concentrated PRP, this is then diluted back to 6 ml and will produce a diluted PRP solution with approximately $2400 \times 10^9$ platelets per litre (6× baseline). Therefore, the concentration of platelets in the PRP portion prior to adding authologous thrombin is typically between 4 and 6 times the baseline platelet level in the whole blood, preferably 6 times.

The optimal level of platelets in the PRP prior to addition of thrombin is envisaged to be approximately $600 \times 10^9$ to $1400 \times 10^9$ platelets per litre. Preferably approximately $600 \times 10^9$ to $1200 \times 10^9$ platelets per litre, approximately $600 \times 10^9$ to $1000 \times 10^9$ platelets per litre, approximately $600 \times 10^9$ to $800 \times 10^9$ platelets per litre, approximately $800 \times 10^9$ to $1400 \times 10^9$ platelets per litre, approximately $800 \times 10^9$ to $1200 \times 10^9$ platelets per litre, or approximately $800 \times 10^9$ to $1000 \times 10^9$ platelets per litre. Thus, the method of the invention includes providing a PRP sample with an optimal level of platelets at step iii), prior to addition of thrombin (and optionally ascorbic acid).

The density of platelets in the Arthrex® Angel® System PRP compared to whole blood at 2% and 7% haematocrit settings and compared with other commercially available machines are provided in Table 2 of Degen et al (2017) referenced above.

According to the first aspect of the invention the wound treatment composition comprises a platelet level of 200 to $2,600 \times 10^9$ platelets per litre, preferably 600 to $2,400 \times 10^9$ platelets per litre, more preferably 1,000 to $2,000 \times 10^9$ platelets per litre.

The wound treatment composition produced according to the first aspect of the invention comprises a final haematocrit level from 0.5 to 10%, or from 1 to 8%. In an embodiment the wound treatment composition produced according to the first aspect of the invention comprises a final haematocrit level of from 0.5 to 5%, from 0.5 to 4%, from 0.5 to 3% or from 0.5 to 2%. In a further embodiment the wound treatment composition produced according to the first aspect of the invention comprises a final haematocrit level of from 4 to 10%, from 4 to 9%, from 4 to 8%, from 4 to 7% or from 4 to 6%.

According to the invention autologously produced thrombin is combined with the PRP. The thrombin acts as an agonist to activate the platelets in the PRP sample which results in the release of growth factors. These growth factors may therefore be present within the wound treatment composition of the invention, non-limiting examples of the growth factors present include platelet-derived growth factor (PDGF-AB), transforming growth factor beta 1 (TGF-B1), insulin-like growth factors (IGF-1 IGF2), vascular endothelial growth factor (VEGF), platelet-derived angiogenesis factor (PDAF), platelet-derived epidermal growth factor (PDEGF), platelet factor 4 (PF-4), acidic fibroblast growth factor (FGF-A), basic fibroblast growth factor (FGF-B), transforming growth factor α (TGF-A), β thromboglobulin-related proteins (BTG), thrombospondin (TSP), fibronectin, von Willinbrand's factor (vWF), fibropeptide A, fibrinogen, albumin, plasminogen activator inhibitor 1 (PAI-1), osteonectin, regulated upon activation normal T cell expressed and presumably secreted (RANTES), gro-α, vitronectin, fibrin D-dimer, factor V, antithrombin III, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), and combinations thereof. These growth factors act synergistically to help promote wound healing.

A second aspect on the invention comprises a wound treatment composition obtainable by the method according to the first aspect of the invention.

A particular feature of the second aspect of the invention is a wound treatment composition comprising platelet rich plasma (PRP), thrombin and ascorbic acid, wherein the composition comprises a platelet level of greater than $200 \times 10^9$ platelets per litre, or greater than $400 \times 10^9$ platelets per litre, or greater than $600 \times 10^9$ platelets per litre, or greater than $800 \times 10^9$ platelets per litre, or greater than $1,000 \times 10^9$ platelets per litre.

In an embodiment of the composition according to the second aspect of the invention the PRP and thrombin are produced from a whole blood sample obtained from a single individual.

The wound treatment composition of the invention may be for use in the treatment of wounds. In a particular embodiment the wound treatment composition of the invention may be for use in the treatment of acute or chronic wounds.

The present inventors have found that a wound treatment composition according to the invention and produced from a PRP sample having a lower haematocrit level, for example between 1 to 5%, is effective in treating chronic wounds. More specifically a wound composition produced from a PRP with a haematocrit level of approximately 2% is surprisingly particularly effective for use in treating chronic wounds. As such an embodiment of the wound treatment composition of the invention may be produced from a PRP sample having a haematocrit level of between 1 to 5%, preferably 2%. Thus in an embodiment, a wound treatment composition formed from a PRP sample having a haematocrit level of between 1 to 5%, preferably 2% may be for use in treating chronic wounds in a patient in need thereof. As used herein the term "chronic wound" refers to a wound which does not progress through the normal phases of wound healing and often remains in the inflammation stage of healing. Non-limited examples of chronic wounds that may occur, and which would benefit from and thus may be treated with the compositions of the invention, include diabetic foot ulcers, venous leg ulcers, and pressure ulcers.

Further a wound treatment composition according to the invention produced from a PRP sample having a higher haematocrit level, for example between 5 to 10%, is effective in treating acute wounds. More specifically a wound composition produced from a PRP with a haematocrit level of approximately 8% is particularly effective for use in treating acute wounds. As such, an embodiment of the wound treatment composition according to the invention may be produced from a PRP sample having a haematocrit level of between 5 to 10%, preferably 8%. Thus in an embodiment, a wound treatment composition formed from a PRP sample having a haematocrit level of between 5 to 10%, preferably 8% may be for use in treating acute wounds in a patient in need thereof. As used herein the term "acute wound" is used to refer to an injury or damage that occurs suddenly rather than over time. A chronic wound may be induced into an acute wound by undergoing processes such as debridement, wherein dead or damaged tissue is removed from a wound to reveal healthy tissue. This exposes the wound to the blood and thus stimulates natural healing. These processes are commonly used during chronic wound treatment and the skilled person will be aware of appropriate methods.

The wound treatment composition of the invention preferably solidifies into a gel consistency once produced. Thus, a mould may be used to tailor the shape of the gel to the wound to be treated or it can be cut to a specific size or shape depending on the wound to be treated and the preference of the clinician. Since the wound treatment composition of the present invention has a more stable structure than previous compositions, it is easier to cut or mould the gel to tailor it to a particular wound.

An embodiment of the invention relates to a method of treating a wound by applying a wound treatment composition of the present invention. This method may comprise multiple applications of wound treatment compositions over the course of treatment. For example, a wound may undergo debridement followed by application of a wound treatment composition produced from a PRP sample having a higher haematocrit level, for example between 5 to 10%. This wound may undergo subsequent treatment by applying a wound treatment composition produced from a PRP sample having a lower haematocrit level, for example between 1 to 5%. A further aspect of the present invention is a method of treating wounds in a subject by administering a wound treatment composition obtainable by the method according to the first aspect of the invention. Thus, the method of treating wounds in a subject according to the invention may comprise the following steps;
  i) obtaining a whole blood sample from the subject to be treated,
  ii) fractionating a whole blood sample into multiple samples including a platelet rich plasma (PRP) sample, a platelet poor plasma (PPP) sample and a erythrocyte sample, wherein the PRP sample has a haematocrit level of 1-10%,
  iii) processing a portion of the PPP and/or PRP sample to facilitate cleavage of autologous pro-thrombin present in the PPP and/or PRP to produce autologous thrombin, and
  iv) combining the PRP sample with a portion of the PPP sample and a portion of the thrombin produced in step (iii) to produce the wound treatment composition, wherein the wound treatment composition comprises a platelet level of greater than $600 \times 10^9$ platelets per litre, and
  v) applying the wound treatment composition to the wound of the subject to be treated; and wherein step iii) is performed at a temperature of less than 15° C.

The method of treating a wound according to the present invention may involve initially debriding a chronic wound to expose a clean wound bed, effectively converting it to an acute wound, or initially treating an acute wound, with the wound treatment composition of the invention produced from a PRP sample of high haematocrit, for example 8%. Then, in following treatment steps, when the initial acute phase of the wound healing is over and the wound may be considered chronic, the method of the invention may then comprise applying the wound treatment composition of the invention produced from a PRP composition having a lower haematocrit, for example 2%. Multiple applications of this second stage may be made as appropriate until satisfactory healing of the wound has taken place.

Thus, a further embodiment of the present invention is a method of treating acute wounds in a subject by administering a wound treatment composition according to the invention produced from a PRP sample having a haematocrit level of 8%. Accordingly, a further embodiment of the present invention is a method of treating chronic wounds in a subject by administering a wound treatment composition according to the invention produced from a PRP sample having a haematocrit level of 2%.

A further aspect of the present invention is the use of a wound treatment composition in the manufacture of a medicament for the treatment of wounds, wherein the wound treatment composition is obtainable by the following method;
  i) fractionating a whole blood sample into multiple samples including a platelet rich plasma (PRP) sample, a platelet poor plasma (PPP) sample and a erythrocyte sample, wherein the PRP sample has a haematocrit level of 1-10%,
  ii) processing a portion of the PPP and/or PRP sample to facilitate cleavage of autologous pro-thrombin present in the PPP and/or PRP to produce autologous thrombin, and
  iii) combining the PRP sample with a portion of the PPP sample and a portion of the thrombin produced in step (ii) to produce the wound treatment composition; and wherein step ii) is carried out at a temperature of less than 15° C.

The invention also provides a wound treatment composition according to the second aspect for use in medicine, in particular for use in treating chronic or acute wounds, as set out herein.

All embodiments described in relation to earlier aspects of the invention are intended to be equally applicable to the preceding aspect of the invention, where appropriate.

The following examples illustrate the invention;

EXAMPLE 1

The following example outlines the steps taken when treating a wound, for example in a diabetic patient.

Stage 1

A PRP with a haematocrit level of 8% is produced for use in the first treatment. Wounds are 'surgically freshened' with surgical debridement of necrotic tissue to expose a fresh acute wound base. The wound treatment composition is produced according to the following formulation. This formulation is designed to be adjusted volumetrically and is doubled in volume to treat wounds of over >7000 mm$^3$.

i. 5 mls PRP processed from 52 mL of whole blood. The PRP contains 5-6× platelet concentration found in the whole blood sample
  ii. Add 0.75 mL ascorbic acid 500 mg/5 ml USP
  iii. Add 2 mL autologous thrombin to activate PRP/ascorbic acid fluid to gel.

The first treatment contains concentrated platelets and large 'dose' of leucocytes. This stage may be referred to as the hyperstimulation treatment. A semi-occlusive dressing such as Opsite may be used to cover the gel and wound.

Stage 2

The second treatment is performed after 48 hours. For the second treatment and subsequent treatments a PRP with a haematocrit level of 2% is used. The subsequent treatments are conducted weekly/every 7 days. Using a 2% haematocrit level >98% leukocytes are removed from the PRP and the wound treatment composition is produced according to the following formulation.

i. 5 mL PRP processed from 52 mL of whole blood. The PRP contains 5-6× platelet concentration found in the whole blood sample
  ii. Add 0.75 mL ascorbic acid 500 mgs/5 ml USP
  iii. Add 2 mL autologous thrombin to activate PRP/ascorbic acid fluid to gel. If the wound does not show >30% wound closure improvement per week, the wound should be treated using the acute formulation with a haematocrit level of 8%.

The approach allows repeatable and robust treatment of chronic wounds in a clinical setting.

EXAMPLE 2

In a clinical setting 18 wounds treated in 15 patients. 5 had extensive tissue loss with exposed bone/tendon/cartilage; 3 on renal replacement therapy; 4 had significant peripheral neuropathy; 4 had deep osteomyelitis; 1 had severe nutritional deficiency related to an eating disorder. Average wound volume at commencement of treatment: 8203.3 mm$^3$ (range 141.3-41257.2 mm$^3$). The wounds were treated using the methodology outlined in example 1. Average wound volume at completion of PRP treatment: 2783.2 mm$^3$ (range 0.5-28809 mm$^3$). Average reduction in wound volume at completion of treatment: 75%. Total number of days to >90% wound healing after commencing PRP treatment: 17.9 days (range 6-40 days). Post treatment surgical intervention was required in 1 patient who went on to major amputation; the rest were discharged without further intervention.

Figure 1:
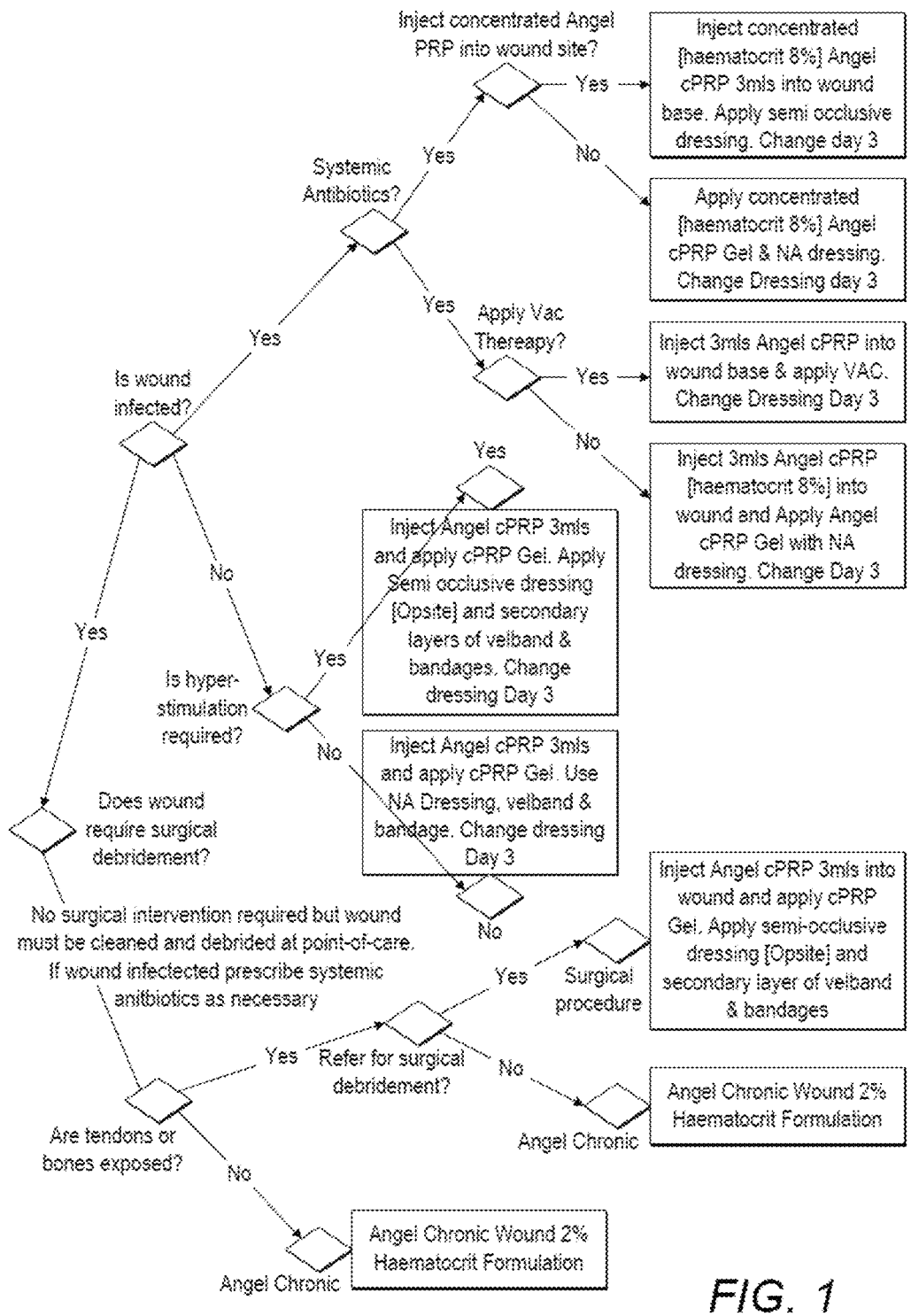
FIG. 1 shows a flow chart which exemplifies the steps taken during the treatment of a wound.
Figure 2:
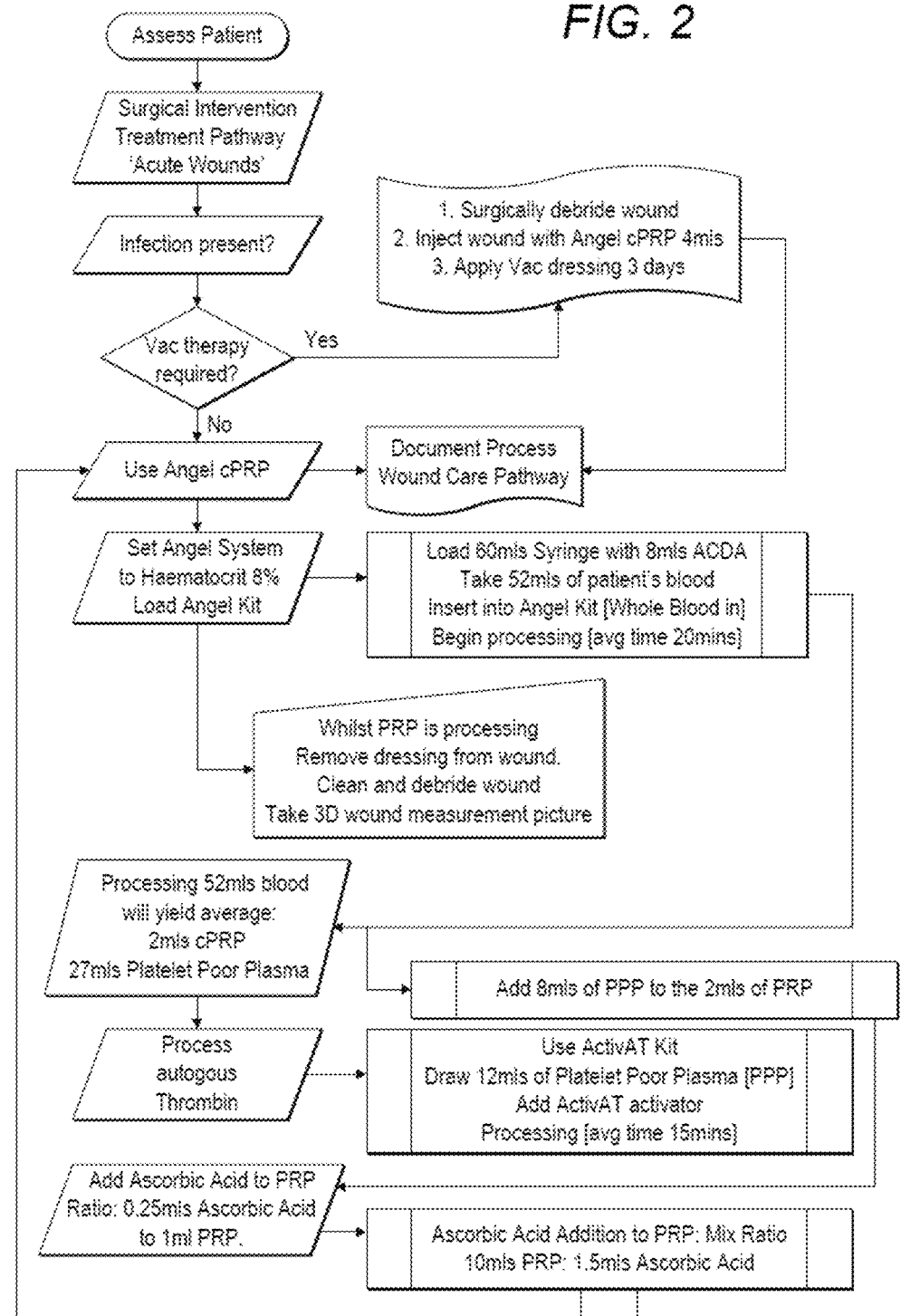
FIG. 2 shows a flow chart which exemplifies the steps taken for the treatment of a wound classified as acute.
Figure 2:
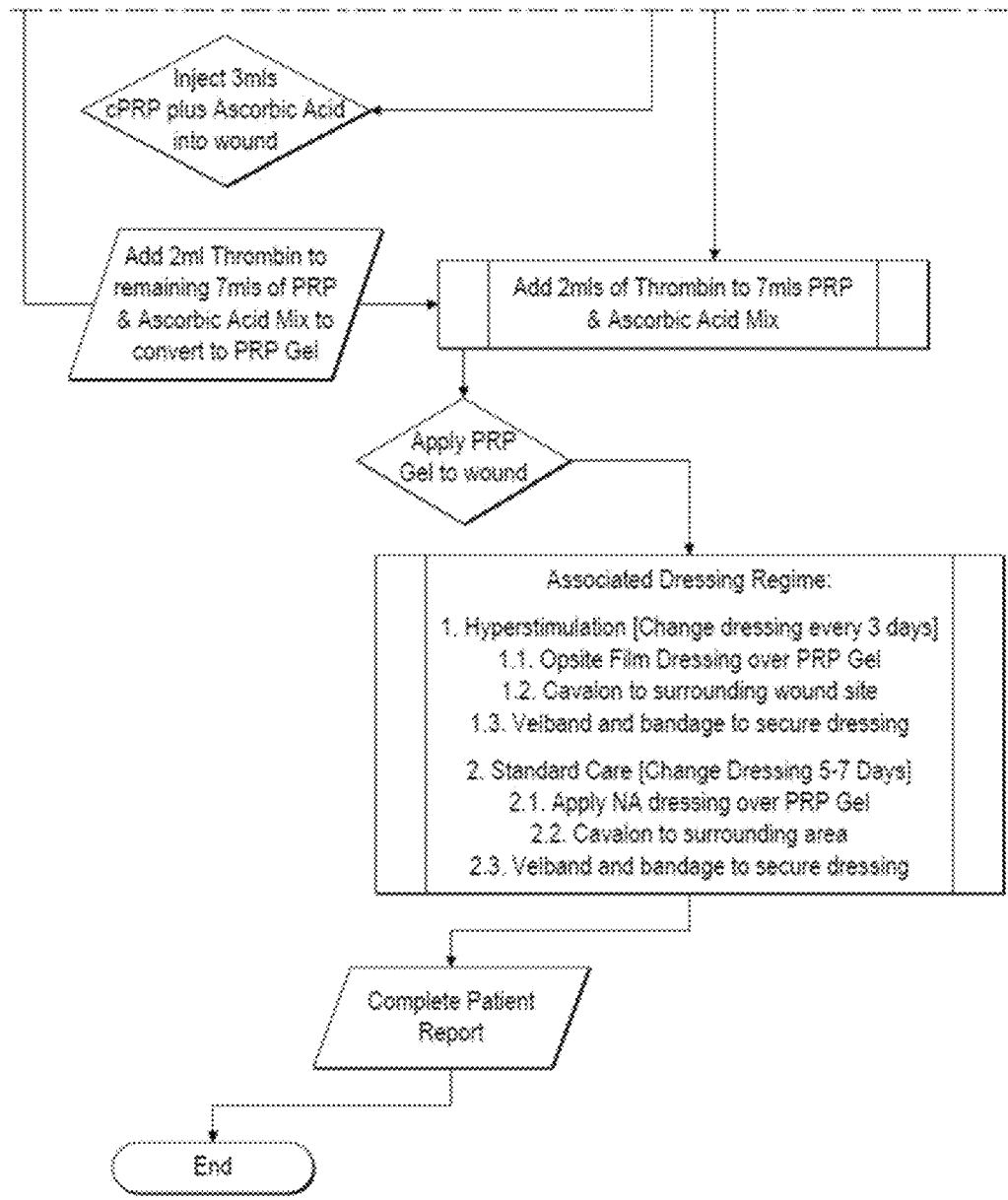
Figure 3:
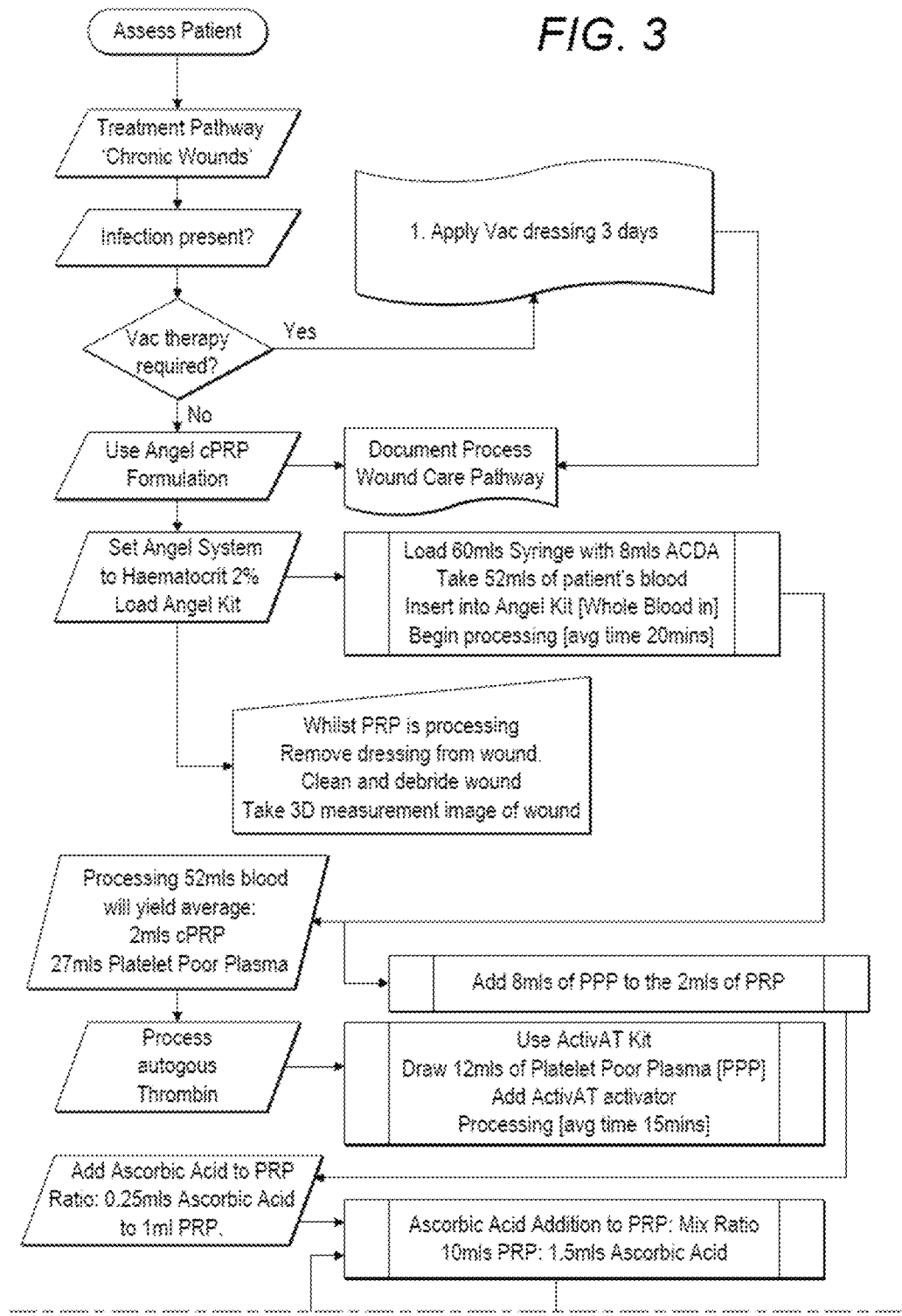
FIG. 3 shows a flow chart which exemplifies the steps taken for the treatment of a wound classified as chronic.
Figure 3:
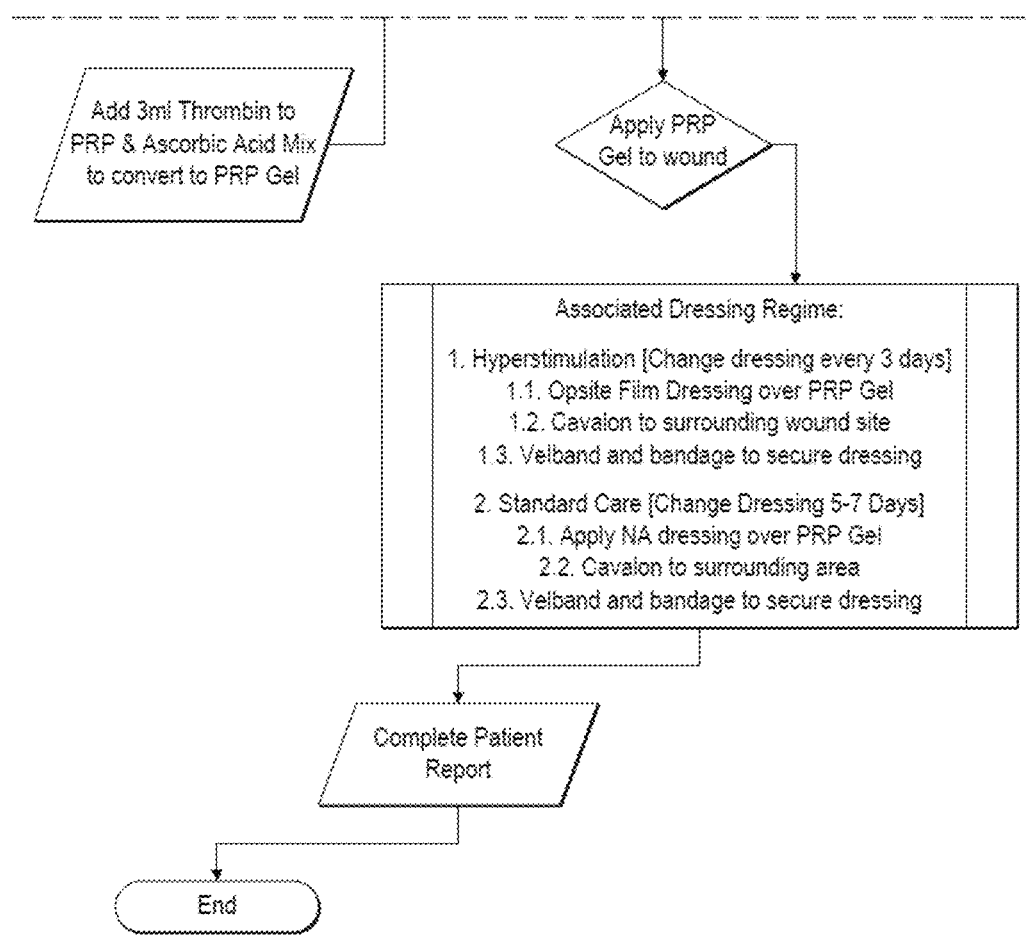
Figure 4:
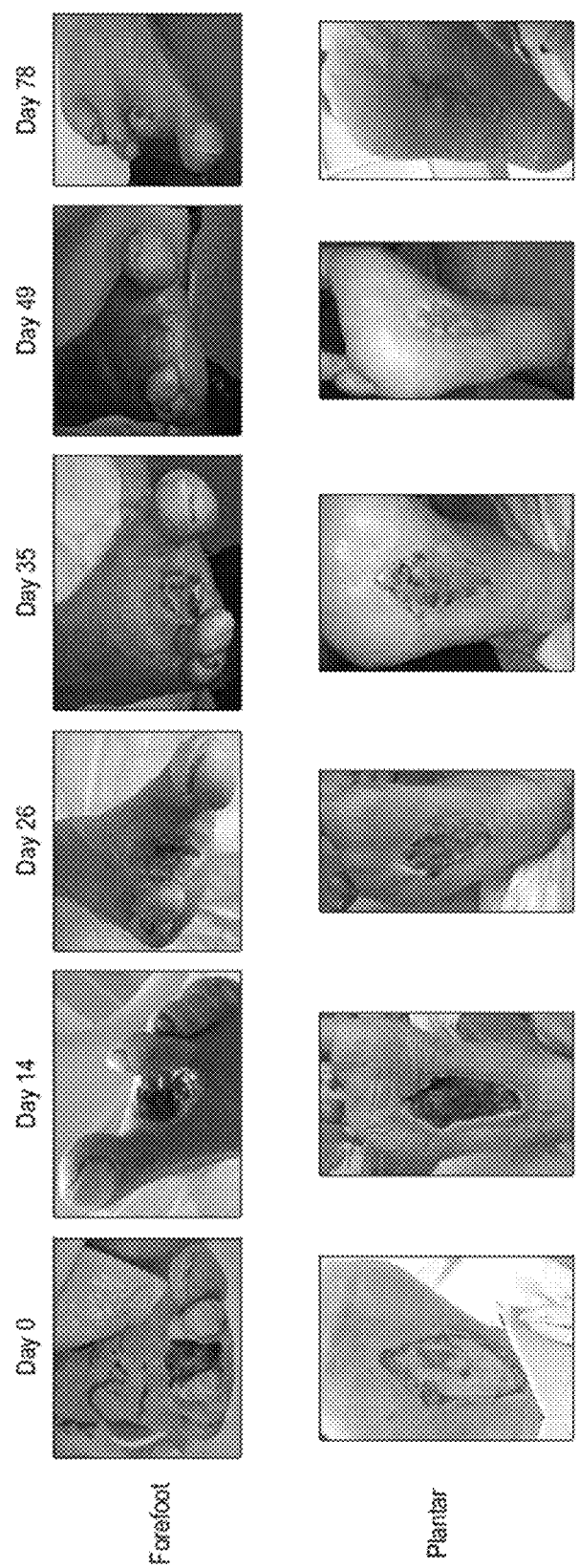
FIG. 4 shows examples of patient wounds which were treated using the wound treatment composition using the protocol outlined in example 1.

FIG. 4 shows examples of patient wounds which were treated in this study and Table 1 details the reduction in wound volume over the course of treatment and the number of days taken for <90% wound healing.

TABLE 1

| Patient No. | Area of wound at commencement of treatment (mm$^3$) | Number of treatments | Size of wound at completion of PRP treatment (mm$^3$) | Reduction of wound at completion of treatment | % Change | Total number of days to >90% wound healing |
|---|---|---|---|---|---|---|
| 1 | 7253.8 | 6 | 2255.3 | −4998.5 | −1407.8 | 33 |
| 2 | 23334.8 | 3 | 5119 | −18215.7 | −78.1% | 9 |
| 3 | 384.4 | 4 | 168 | −216.2 | −50.1 | 10 |
| 4 | 41257.9 | 5 | 28809 | −12448.9 | −69.82 | 17 |
| 5 | 5178.9 | 2 | 1440.43 | −3738.5 | −72.2 | 13 |
| 6 | 141.3 | 2 | 1.9 | 139.4 | −98.65 | 8 |
| 7 (heel) | 7815.6 | 3 | 3001.1 | −4814.5 | −61.6 | 8 |
| 7 (toes) | 756.6 | 4 | 0.5 | −756.1 | −99.9 | 13 |
| 8 | 9873.7 | 7 | 131 | −9742.4 | −98.7 | 40 |
| 9 | 27047.7 | 6 | 2598.4 | −24449.3 | −96 | 26 |
| 10 | 10004 | 4 | 2098.6 | −7905.4 | −77.6 | 18 |
| 11 (left leg) | 96.8 | 5 | 1.3 | −95.5 | −98.6 | 35 |
| 11 (right Leg) | 231.5 | 5 | 2.5 | −229 | −98.9 | 35 |
| 12 heel | 2410.4 | 2 | 467.4 | −1943 | −80.6 | 6 |
| 12 plantar | 425 | 2 | 12.6 | −412.4 | −72.7 | 6 |
| 13 | 3669.4 | 4 | 2623.1 | −1046.3 | −73.4 | 13 |
| 14 | 1817.5 | 2 | 409.7 | −1407.8 | −77.5 | 7 |
| 15 | 5958.7 | 4 | 959 | −4999.7 | −83.9 | 26 |

EXAMPLE 3

A diabetic patient underwent surgical debridement of a wound and removal of osteomyelitis in the heel region. This wound was then treated with the wound treatment composition of the present invention. Three treatments were administered over 14 days.

Figure 5:
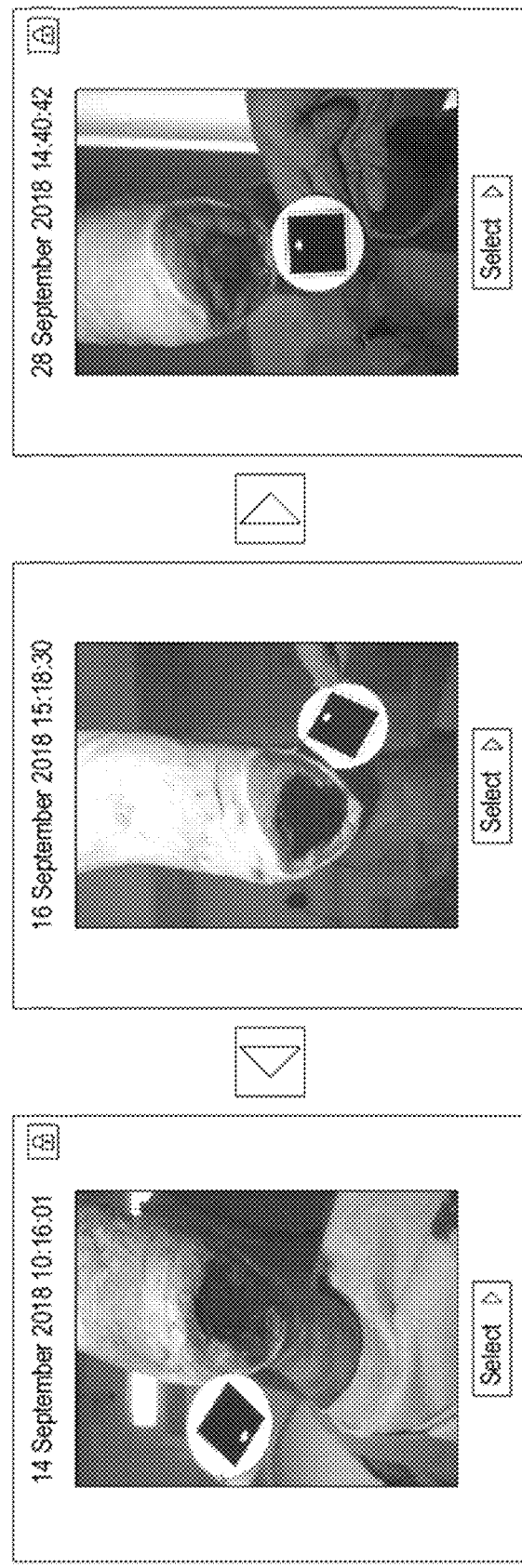
FIG. 5 shows a wound in the heel of diabetic patient, which has been treated using the protocol outlined in example 1.

Over the 14 days the decrease in curved volume was −36581.2 mm$^3$ (−90.7%). The volume change was −417.3 mm$^3$ (−30.8%) which shows an increase in volume as the wound granulates and regenerates tissue to close the wound. The decrease in the wound area was −1051.1 mm$^2$ (−25.8%). Image of the wound healing over the course of the treatment are shown in FIG. 5.

The wound treatment composition was produced according to the invention. The below table demonstrates the effect of performing the conversion of prothrombin to thrombin at a temperature of less than 15° C. on some of the key characteristics of the wound care treatment.

|  | Chronic gel produced with no cooling step | Chronic gel produced with cooling step |
|---|---|---|
| PRP volume | 6 mL | 6 mL |
| Platelet conc | 2.75-4.2× | 2.75-4.2× |
| Neutrophil conc | 0.3× | 0.3× |
| White blood cells | 2× | 2× |
| Ascorbic acid | 75 mg | 75 mg |
| Human thrombin 50 ng + CaCl$_2$ 16.6 mg/mL | 2 mL | 2 mL |
| Time to hold shape when removed from mould | <1 minute | 10 mins |

The platelet, neutrophil and white blood cell concentrations are expressed as a factor of the starting level.

The invention claimed is:

1. A method of making a wound treatment composition, wherein the method comprises;
   i) fractionating, in a centrifuge, a human whole blood sample into multiple samples including a platelet rich plasma (PRP) sample, a platelet poor plasma (PPP) sample and an erythrocyte sample, wherein the PRP sample has a haematocrit level of 1-10%,
   ii) removing the PRP sample and the PPP sample from the centrifuge,
   iii) processing a portion of the PPP sample to facilitate cleavage of autologous pro-thrombin present in the PPP sample to produce autologous thrombin, and
   iv) combining the PRP sample with a portion of the PPP sample and a portion of the thrombin produced in step (iii) to produce the wound treatment composition; and wherein the processing step to facilitate cleavage of the autologous pro-thrombin from the PPP sample to produce autologous thrombin is carried out at a temperature of less than 15° C., and
   wherein the wound treatment composition provides for prolonged release of growth factors, and has a final hematocrit level of 0.5 to 10% and
   wherein the wound treatment composition is suitable for use by 35 minutes from obtaining the human whole blood sample.

2. The method of claim 1, wherein step iv) is carried out at a temperature of less than 15° C.

3. The method according to claim 1, further comprising the step of adding ascorbic acid to the wound treatment composition contemporaneously with, prior to, or after addition of the thrombin.

4. The method according to claim 1, wherein the PRP sample has a haematocrit level of 8%.

5. The method according to claim 1, wherein the PRP sample has a haematocrit level of 2%.

6. The method according to claim 1, wherein the wound treatment composition comprises a platelet level of 600 to 2,400×10$^9$ platelets per litre.

7. The method of claim 1, wherein the wound treatment composition exhibits a consistency that allows the composition to maintain its shape for approximately ten minutes.

8. The method of claim 1, wherein the temperature is 2-12° C.

9. The method of claim 1, wherein the temperature is 2-10° C.

* * * * *